United States Patent
Takagi et al.

(10) Patent No.: US 9,155,710 B2
(45) Date of Patent: *Oct. 13, 2015

(54) ROPINIROLE-CONTAINING PATCH AND PACKAGE THEREOF

(75) Inventors: Yuka Takagi, Tsukuba (JP); Naoyuki Uchida, Tsukuba (JP); Yasunari Michinaka, Tsukuba (JP)

(73) Assignee: Hisamitsu Pharmaceutical Co., Inc., Tosu-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/123,163

(22) PCT Filed: May 23, 2012

(86) PCT No.: PCT/JP2012/063160
§ 371 (c)(1),
(2), (4) Date: Nov. 29, 2013

(87) PCT Pub. No.: WO2012/165253
PCT Pub. Date: Dec. 6, 2012

(65) Prior Publication Data
US 2014/0112974 A1 Apr. 24, 2014

(30) Foreign Application Priority Data
May 31, 2011 (JP) ................ 2011-122527

(51) Int. Cl.
*A61K 9/70* (2006.01)
*A61K 31/4045* (2006.01)

(52) U.S. Cl.
CPC .......... *A61K 9/7038* (2013.01); *A61K 9/7053* (2013.01); *A61K 31/4045* (2013.01)

(58) Field of Classification Search
None
See application file for complete search history.

(56) References Cited

U.S. PATENT DOCUMENTS

| | | | |
|---|---|---|---|
| 5,807,570 A * | 9/1998 | Chen et al. ................ | 424/449 |
| 8,802,134 B2 | 8/2014 | Higo et al. | |
| 2005/0031547 A1 | 2/2005 | Tamarkin et al. | |
| 2007/0207222 A1 * | 9/2007 | Yu et al. ................ | 424/725.1 |
| 2008/0286364 A1 * | 11/2008 | Ogiwara et al. ........... | 424/489 |
| 2010/0034838 A1 | 2/2010 | Staniforth et al. | |
| 2011/0028880 A1 * | 2/2011 | Uchida et al. ............... | 602/48 |
| 2011/0165247 A1 | 7/2011 | Breitenbach | |
| 2011/0195109 A1 * | 8/2011 | Michinaka et al. .......... | 424/448 |
| 2012/0052113 A1 | 3/2012 | Uchida et al. | |
| 2012/0090275 A1 | 4/2012 | Uchida et al. | |
| 2013/0165875 A1 | 6/2013 | Choi et al. | |
| 2014/0112974 A1 | 4/2014 | Takagi et al. | |
| 2014/0170205 A1 | 6/2014 | Uchida et al. | |
| 2014/0186428 A1 | 7/2014 | Aida et al. | |

FOREIGN PATENT DOCUMENTS

| | | |
|---|---|---|
| CA | 2857156 | 6/2013 |
| EP | 2561865 A2 | 2/2013 |
| EP | 2749274 A1 | 7/2014 |
| JP | 63-093714 | 4/1988 |
| JP | 11 506462 | 6/1999 |
| JP | 11/506462 | 6/1999 |
| JP | 2001 518058 | 10/2001 |
| JP | 2001-518058 | 10/2001 |
| JP | 2002/504070 | 2/2002 |
| JP | 2007 516265 | 6/2007 |
| JP | 2009 518376 | 5/2009 |
| JP | 2009-518376 | 5/2009 |
| WO | 96/39136 | 12/1996 |
| WO | 97/10812 | 3/1997 |
| WO | 97/11696 | 4/1997 |
| WO | 2009 107478 | 9/2009 |
| WO | 2009/107478 A1 | 9/2009 |
| WO | 2009 107479 | 9/2009 |
| WO | 2010 123103 | 10/2010 |
| WO | WO 2010/134433 A1 | 11/2010 |
| WO | 2012/165254 A1 | 12/2012 |
| WO | 2013/081102 A1 | 6/2013 |

OTHER PUBLICATIONS

International Search Report Issued Jul. 10, 2012 in PCT/JP12/063160 Filed May 23, 2012.
U.S. Appl. No. 14/123,148, filed Nov. 29, 2013, Uchida, et al.
U.S. Appl. No. 14/317,976, filed Jun. 27, 2014, Yoshizaki, et al.
EESR, Office Action issued Aug. 8, 2014 in EP Patent Application No. 14174708.9-1460.
Marcel Dekker, "Pharmaceutical skin penetration enhancement," edited by KA Walters and J. Hadgraft, (The United States), vol. 59, 1993, pp. 243-267. For example Japanese Patent Application Publication No. Sho 63-93714.
Notification of Reasons for Refusal, Patent Application No. 2013-137147, drafting date: Aug. 15, 2013. English translation.

* cited by examiner

*Primary Examiner* — Brian Kwon
*Assistant Examiner* — Jennifer A Berrios
(74) *Attorney, Agent, or Firm* — Oblon, McClelland, Maier & Neustadt, L.L.P.

(57) ABSTRACT

A ropinirole-containing patch comprises an adhesive agent layer and a support layer, the adhesive agent layer containing ropinirole and/or a pharmaceutically acceptable salt thereof, wherein
a content of the ropinirole and/or the pharmaceutically acceptable salt thereof in terms of free ropinirole in the adhesive agent layer is 5 to 13.2% by mass relative to a total mass of the adhesive agent layer.

18 Claims, 6 Drawing Sheets

ROPINIROLE-CONTAINING PATCH AND PACKAGE THEREOF

This application is a National Stage of PCT/JP12/063160 filed May 23, 2012 and claims the benefit to JP 2011-122527 filed May 31, 2011.

TECHNICAL FIELD

The present invention relates to a ropinirole-containing patch and a package thereof.

BACKGROUND ART

Conventionally, as a Parkinson's disease treatment, L-Dopa therapy has been known, in which L-Dopa known as a therapeutic preparation for the disease is administered to supplement dopamine. Nevertheless, the L-Dopa therapy has problems: for example, long-term continuous administration is required, but the long-term continuous administration gradually reduces the drug effect, and a diurnal variation in the symptoms is produced very frequently. Hence, ropinirole was developed as a drug to solve such problems with the L-Dopa therapy. Recently, for the purpose of disease treatments for Parkinson's disease, restless legs syndrome, and the like, various studies have been conducted on preparations which contain ropinirole and/or pharmaceutically acceptable salts thereof.

For example, International Application Japanese-Phase Publication Nos. 2009-518376 (PTL 1) and 2007-516265 (PTL 2) each disclose a composition for topical administration, containing ropinirole, as an external preparation such that side effects in the stomach and intestines can be avoided. Furthermore, efforts have been made also to study transdermal preparations because it is easy to remove a transdermal preparation when a side effect occurs and it is easier to adjust the amount of the drug to be administered. For example, International Application Japanese-Phase Publication Nos. 2001-518058 (PTL 3) and Hei 11-506462 (PTL 4) each disclose, as a transdermal preparation containing ropinirole, a patch including a support layer and an adhesive agent layer containing ropinirole. However, the patches described in PTLs 3 and 4 above have problems that the skin permeability of ropinirole still has not been sufficient, making it difficult to keep the ropinirole concentration in the plasma at a sufficiently high level.

Meanwhile, the drug is normally distributed in the market in the form of an acid addition salt because of the handleability and the stability. When the drug in the form of acid addition salt is directly used in a transdermal preparation or the like, the skin permeability of the drug tends to be reduced. It is known that the drug is preferably used in a free form from the viewpoint of skin permeability. For example, International Publication No. WO2009/107478 (PTL 5) discloses a patch including an adhesive agent layer containing: ropinirole in a free form (free ropinirole) and a metal salt produced by a reaction of a ropinirole acid addition salt and a metal-ion containing desalting agent in an equivalent mole or less to the acid addition salt; and an adhesive base free of a hydroxyl group and a carboxyl group.

CITATION LIST

Patent Literatures

[PTL 1] International Application Japanese-Phase Publication No. 2009-518376

[PTL 2] International Application Japanese-Phase Publication No. 2007-516265

[PTL 3] International Application Japanese-Phase Publication No. 2001-518058

[PTL 4] International Application Japanese-Phase Publication No. Hei 11-506462

[PTL 5] International Publication No. WO2009/107478

SUMMARY OF INVENTION

Technical Problem

The present inventors have made efforts to produce a transdermal preparation by desalting a ropinirole acid addition salt during the production or during the formulation of the preparation so as to improve the skin permeability of ropinirole as described in PTL 5 above. As a result, the inventors have found out that when a content of the ropinirole acid addition salt in an adhesive agent layer is 5% by mass (4.4% by mass in terms of free ropinirole) as described in Examples of the literature, there is a problem that the amount of ropinirole permeated through the skin is not sufficient yet. Moreover, the present inventors have found out that when the content of ropinirole and/or a pharmaceutically acceptable salt thereof in the adhesive agent layer is adjusted in such a manner that a sufficient amount of ropinirole is permeated through the skin, on the other hand, this makes it difficult to keep the adhesive properties of the patch, and reduces the adhesiveness of the patch. Furthermore, the inventors have found out that the cause is, surprisingly, the ropinirole free form (free ropinirole), despite being solid at room temperature, having actions of plasticizing the adhesive base contained in the adhesive agent layer and reducing the aggregation ability of the adhesive agent layer.

The present invention has been made in view of the above-described problems of the conventional techniques. An object of the present invention is to provide a ropinirole-containing patch having an excellent skin permeability of ropinirole and a sufficient adhesiveness, and a package of the ropinirole-containing patch, which has an excellent ropinirole stability over time.

Solution to Problem

The present inventors have conducted earnest study to achieve the above object. As a result, the present inventors have found that in a ropinirole-containing patch comprising an adhesive agent layer and a support layer, the adhesive agent layer containing ropinirole and/or a pharmaceutically acceptable salt thereof, when a content of the ropinirole and/or the pharmaceutically acceptable salt thereof in terms of free ropinirole in the adhesive agent layer is within a specific range, an excellent skin permeability of ropinirole is demonstrated, and a sufficient adhesiveness is achieved. Furthermore, the present inventors have found out that by sealing and storing such a ropinirole-containing patch together with a deoxidizer, the ropinirole stability over time is further improved. These findings have led the inventors to complete the present invention.

Specifically, a ropinirole-containing patch of the present invention is a ropinirole-containing patch comprising an adhesive agent layer and a support layer, the adhesive agent layer containing ropinirole and/or a pharmaceutically acceptable salt thereof, wherein a content of the ropinirole and/or the pharmaceutically acceptable salt thereof in terms of free ropinirole in the adhesive agent layer is 5 to 13.2% by mass relative to a total mass of the adhesive agent layer.

In the ropinirole-containing patch of the present invention, the adhesive agent layer preferably further contains 5 to 50 parts by mass of at least one compound selected from the group consisting of benzyl alcohol, oleyl alcohol, octyldodecanol, and dimethyl isosorbide, per 100 parts by mass of the ropinirole and/or the pharmaceutically acceptable salt thereof in terms of free ropinirole.

Moreover, in the ropinirole-containing patch of the present invention, the adhesive agent layer preferably contains 10 to 150 parts by mass of at least one compound selected from the group consisting of isopropyl myristate, isopropyl palmitate, lauryl alcohol, glycerol monooleate, propylene glycol monolaurate, polyoxyethylene sorbitan monooleate, and lauric acid diethanolamide, per 100 parts by mass of the ropinirole and/or the pharmaceutically acceptable salt thereof in terms of free ropinirole.

Further, in the ropinirole-containing patch of the present invention, the adhesive agent layer preferably further contains 15 to 35% by mass of a rubber-based adhesive relative to the total mass of the adhesive agent layer, and preferably further contains 0.5 to 1.0 mol of sodium hydroxide per 1 mol of the ropinirole and/or the pharmaceutically acceptable salt thereof in terms of free ropinirole.

A package of the present invention comprises the ropinirole-containing patch of the present invention and a deoxidizer together sealed in a packaging bag.

Advantageous Effects of Invention

The present invention makes it possible to provide a ropinirole-containing patch having an excellent skin permeability of ropinirole and a sufficient adhesiveness, and a package of the ropinirole-containing patch, which has an excellent ropinirole stability over time.

DESCRIPTION OF EMBODIMENTS

Hereinafter, preferred embodiments of the present invention will be described in detail with reference to the drawings. Note that, in the following description and drawings, the same or corresponding components are denoted by the same reference symbols, and redundant description thereof is omitted.

Figure 1:
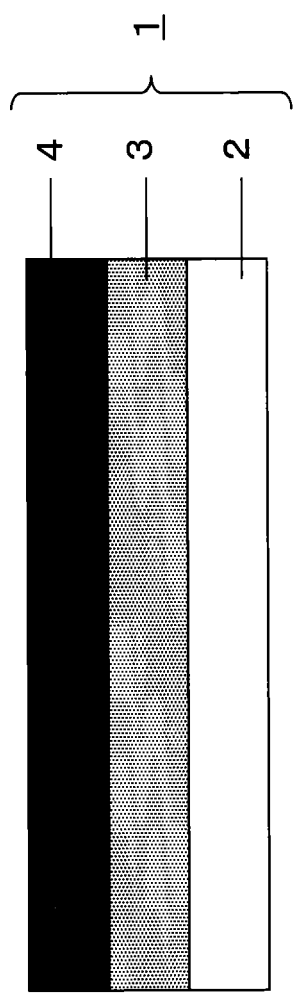
FIG. 1 is a schematic longitudinal cross-sectional view showing a preferred embodiment of a ropinirole-containing patch of the present invention.

FIG. 1 is a schematic longitudinal cross-sectional view showing a preferred embodiment of a ropinirole-containing patch of the present invention. In FIG. 1, a patch 1 comprises: a support layer 2; an adhesive agent layer 3 laminated on the support layer 2; and a release sheet 4 attached on the adhesive agent layer 3. In the present embodiment, when the patch 1 is used, the release sheet 4 is removed for the use of the patch 1. It should be noted that the ropinirole-containing patch of the present invention is not limited to the embodiment showed in FIG. 1. For example, two or more layers of the adhesive agent layers may be laminated, and may be laminated not only on one side of the support layer 2 but on both sides thereof. When multiple adhesive agent layers are present, at least one of them should be the adhesive agent layer 3 according to the present invention.

The material for the support layer 2 is not particularly limited, and ones typically usable as a support layer of a patch can be used as appropriate, which may be elastic or non-elastic. Specific examples of the material include synthetic resins such as polyethylene terephthalate, polyethylenes, polypropylenes, polybutadienes, ethylene vinyl acetate polymers, polyvinyl chlorides, polyesters, nylons, and polyurethanes, and paper materials. Examples of the form of the support layer 2 include a film, a sheet, and laminates thereof; a porous membrane; a foam; and a fabric and a non-woven fabric.

The material for release sheet 4 is not particularly limited, and ones typically usable as a release sheet of a patch can be used as appropriate. Examples of the material include films made of polyesters, polypropylenes, polyethylenes, papers, or laminates thereof. Such films are preferably release-treated, for example, coated with a silicone so as to be easily releasable.

The adhesive agent layer 3 contains at least an adhesive base and ropinirole and/or a pharmaceutically acceptable salt thereof.

Examples of the adhesive base include rubber-based adhesives, acrylic-based adhesives, silicone-based adhesives, and the like. One of these may be used alone, or two or more thereof may be used in combination. Above all, from the viewpoints of a strong aggregation ability and suppressing the action by a ropinirole free form of plasticizing the adhesive bases, at least one of the adhesive bases is preferably a rubber-based adhesive. Examples of the rubber-based adhesive include natural rubbers and synthetic rubbers. From the viewpoints that the formation of a decomposition product of ropinirole (ropinirole analogues) in the adhesive agent layer 3 can be sufficiently suppressed and that the ropinirole stability over time is further improved, more preferable is at least one selected from the group consisting of synthetic rubbers free of a hydroxyl group and a carboxyl group such as a styrene-isoprene-styrene block copolymer (hereinafter abbreviated as "SIS"), isoprene rubber, polyisobutylene (hereinafter abbreviated as "PIB"), a styrene-butadiene-styrene block copolymer (hereinafter abbreviated as "SBS"), styrene-butadiene rubber (hereinafter abbreviated as "SBR"), and polybutenes. Meanwhile, one of these rubber-based adhesives may be used alone, or two or more thereof may be used in combination. Nevertheless, from the viewpoints of having a preferable aggregation ability, demonstrating a preferable adhesion strength in the patch, and further improving the ropinirole stability over time particularly when used in combination with sodium hydroxide, particularly preferably, SIS is used alone, or SIS and PIB are used in combination in a mass ratio (SIS mass:PIB mass) ranging from 9:1 to 1:1.

A content of the rubber-based adhesive(s) is preferably 15 to 35% by mass relative to a total mass of the adhesive agent layer 3. If the content is below the lower limit, this makes it difficult for the adhesive agent layer 3 to have a sufficient aggregation ability in the patch of the present invention containing a high concentration of the ropinirole free form, so that the adhesive base tends to remain on the skin after the patch is applied to and then released from the skin. On the other hand, if the content exceeds the upper limit, the adhesive agent layer 3 becomes too hard, so that the adhesiveness of the patch tends to be reduced.

When the acrylic-based adhesive is used, examples of the acrylic-based adhesive include acrylic-based polymers, and the like, contained in an acrylic acid.acrylic acid octyl ester copolymer, a 2-ethylhexyl acrylate.vinylpyrrolidone copolymer solution, an acrylic acid ester.vinyl acetate copolymer, a 2-ethylhexyl acrylate.2-ethylhexyl methacrylate.dodecyl methacrylate copolymer, a methyl acrylate.2-ethylhexyl acrylate copolymer resin emulsion, an acrylic resin alkanolamine solution listed as adhesives in "Japanese Pharmaceutical Excipients Directory 2000 (edited by Japan Pharmaceutical Excipients Council, published on Apr. 28, 2000, 1st edition)." Above all, commercially available DURO-TAK acrylic adhesive series (manufactured by National Starch and Chemical Company), EUDRAGIT series (manufactured by Higuchi Inc.), or the like is preferably used.

When the silicone-based adhesive is used, a polymer having an organopolysiloxane skeleton is preferably used as the silicone-based adhesive. More preferably, when the polymer having an organopolysiloxane skeleton has hydroxyl groups (for example, silanol groups), at least some of the hydroxyl groups are capped with trimethylsilyl groups. Moreover, the polymer having an organopolysiloxane skeleton further preferably has adhesiveness. Note that a mode of the capping with trimethylsilyl groups include one in which an end silanol group of the polymer having an organopolysiloxane skeleton is end-capped with a trimethylsilyl group. Examples of such a polymer having an organopolysiloxane skeleton include polydimethylsiloxane (such as a polymer designated as MQ according to ASTMD-1418), polymethylvinylsiloxane (such as a polymer designated as VMQ according to ASTMD-1418), polymethylphenylsiloxane (such as a polymer designated as PVMQ according to ASTMD-1418), and the like.

When the acrylic-based adhesive and/or the silicone-based adhesive are used, a total content thereof is preferably 10 to 90% by mass, more preferably 15 to 80% by mass, and particularly preferably 20 to 70% by mass, relative to the total mass of the adhesive agent layer 3 from the viewpoints that the adhesive agent layer 3 is formed favorably and that the skin permeability of the active ingredients is excellent.

The ropinirole contained in the adhesive agent layer 3 may be any one of, or a mixture of two or more of: a free form, a pharmaceutically acceptable salt, and a free form obtained by desalting a pharmaceutically acceptable salt of ropinirole during the production and/or in the preparation thus produced. A content of such ropinirole and/or a pharmaceutically acceptable salt thereof in terms of free ropinirole in the adhesive agent layer 3 has to be 5 to 13.2% by mass. If the content is below the lower limit, an amount of ropinirole permeated through the skin is reduced; furthermore, the amount of ropinirole permeated through the skin cannot be kept in a sufficient amount for a long period, and the ropinirole concentration in the plasma cannot be kept at a high level. On the other hand, if the content exceeds the upper limit, the action by the ropinirole free form of plasticizing the adhesive base(s) is increased, which reduces the aggregation ability of the adhesive agent layer 3 and reduces the adhesiveness of the patch; furthermore, the ropinirole stability over time is reduced, so that ropinirole analogues are likely to be formed.

The pharmaceutically acceptable salt of ropinirole is preferably a ropinirole acid adduct. Examples of the acid include monoprotic acids such as hydrochloric acid, hydrobromic acid, and methanesulfonic acid; and polyprotic acids such as fumaric acid, maleic acid, citric acid, and tartaric acid.

Additionally, when such a ropinirole acid adduct is contained as a raw material of the patch of the present invention in the adhesive agent layer 3, the adhesive agent layer 3 according to the present invention preferably further contains a metal-ion containing desalting agent (neutralizer). When the adhesive agent layer 3 contains the metal-ion containing desalting agent and the ropinirole acid adduct at the time of the production, all or part of the ropinirole acid adduct is desalted during the production process and/or in the preparation thus produced, and a ropinirole free form in a state of free base is obtained. Consequently, when the preparation is applied, the ropinirole free form with a higher tissue absorbability can be made present in the adhesive agent layer 3. Specific examples of the metal-ion containing desalting agent include alkali metal hydroxides such as sodium hydroxide, potassium hydroxide, and magnesium hydroxide. Above all, sodium hydroxide is preferable from the viewpoints of the handling easiness at the time of the production and the ropinirole stability over time which is further improved when the rubber-based adhesive (more preferably SIS) is combined.

When the metal-ion containing desalting agent is contained, the addition may be carried out once during the production steps, or carried out in several times in a divided manner. One of the aforementioned metal-ion containing desalting agents may be added alone, or two or more thereof may be added in combination. Additionally, a content of the metal-ion containing desalting agent is preferably 0.5 to 4 equivalent amounts to the equivalent amount of the acid base of the ropinirole acid adduct from the viewpoint of obviating the decomposition of ropinirole caused by an excessive amount of the metal-ion containing desalting agent.

Meanwhile, if the metal-ion containing desalting agent is added in an equivalent amount exceeding an equivalent mole of the equivalent amount of the acid base of the ropinirole acid adduct, the ropinirole stability over time is reduced, so that a large amount of ropinirole analogues is formed, and tends to cause the coloring of the adhesive agent layer. On the other hand, if the metal-ion containing desalting agent is added in an equivalent amount equal to or less than the equivalent mole, particularly when the rubber-based adhesive (more preferably SIS) is combined, a small amount of ropinirole analogues is formed, and tends not to develop the coloring of the adhesive agent layer. From these viewpoints, the content of the metal-ion containing desalting agent is more preferably 0.5 to 1 equivalent amounts, further preferably 0.6 to 1 equivalent amounts, to the equivalent amount of the acid base of the ropinirole acid adduct. In other words, the adhesive agent layer 3 according to the present invention preferably further contains 0.5 to 1.0 mol, further preferably 0.6 to 1.0 mol, of sodium hydroxide per mol of the ropinirole and/or the pharmaceutically acceptable salt thereof in terms of free ropinirole.

In the desalting (neutralization) reaction of the ropinirole acid adduct, the ropinirole acid adduct reacts with the metal-ion containing desalting agent in the equivalent amount equal to or less than the equivalent mole of the equivalent amount of the acid base of the acid adduct to thereby obtain a ropinirole free form and a metal salt in an equivalent mole or less to the equivalent amount of the acid base of the ropinirole acid adduct. Thus, the adhesive agent layer 3 according to the present invention may further contain such a metal salt. The metal salt is not particularly limited, as long as it is produced by the desalting (neutralization) reaction. The metal salt is determined based on the combination of the ropinirole acid addition salt and the metal-ion containing desalting agent (neutralizer) for desalting the ropinirole acid addition salt. Nevertheless, the metal salt is preferably at least one selected from the group consisting of metal chlorides, metal bromides, metal iodides, and organic acid metal salts. Above all, the metal salt is more preferably at least one selected from the group consisting of sodium chloride, calcium chloride, aluminium chloride, stannous chloride, ferric chloride, magnesium chloride, potassium chloride, sodium citrate, sodium oxalate, sodium tartrate, sodium bromide, and sodium succinate.

In addition, the metal salt produced by the neutralization reaction as described above tends to aggregate and grow as crystals within a short period after the production, when a very small amount of the polar solvent such as water used in the production steps remains in the adhesive agent layer 3. Thus, to suppress crystal aggregation and growth of the metal salt, or disperse the crystals uniformly, the adhesive agent layer 3 according to the present invention more preferably further contains an adsorbent.

The adsorbent is not particularly limited, as long as it is a hygroscopic inorganic and/or organic substance and does not inhibit the effects of the present invention. Generally, examples thereof include inorganic substances and organic substances listed as additives in "Japanese Pharmaceutical Excipients Directory 2000 (edited by Japan Pharmaceutical Excipients Council, published on Apr. 28, 2000, 1st edition)" and described as having hygroscopic properties, dampproofing properties, and adsorptive properties; and aminoalkyl methacrylate copolymers, zinc oxide, and the like which are not described in "Japanese Pharmaceutical Excipients Directory 2000" mentioned above but are known to have hygroscopic properties. One of these may be used alone, or two or more thereof may be used in combination. Examples of such adsorbents include minerals such as talc, kaolin, and bentonite; silicon compounds such as fumed silica (such as AEROSIL (registered trademark)), and hydrous silica; metal compounds such as zinc oxide and dried aluminum hydroxide gel; weak acids such as lactic acid and acetic acid; sugars such as dextrin; and polymers such as polyvinylpyrrolidone, propylene glycol, aminoalkyl methacrylate copolymers, crospovidone, and carboxy vinyl polymers.

When the adsorbent is contained, a content thereof is preferably 0.5 to 50% by mass relative to the total mass of the adhesive agent layer 3. If the content is below the lower limit, there is a tendency that the effects of suppressing the crystal aggregation and growth of the metal salt and uniformly dispersing the crystals are not obtained sufficiently. On the other hand, if the content exceeds the upper limit, the adhesion strength of adhesive agent layer 3 is reduced, and it tends to be difficult to apply the patch.

Moreover, in the patch of the present invention, the adhesive agent layer 3 preferably further contains at least one compound selected from the group consisting of benzyl alcohol, oleyl alcohol, octyldodecanol, and dimethyl isosorbide (hereinafter sometimes referred to as compound (A)). Above all, it is more preferable to further contain octyldodecanol. The present inventors have found out that, in the patch of the present invention, when the adhesive agent layer 3 contains the ropinirole free form in a high concentration, crystals may be formed in the adhesive agent layer 3 over time from the ropinirole free form, and that such crystallization of the ropinirole free form can be suppressed by further incorporating the compound (A) (particularly octyldodecanol) in the adhesive agent layer 3.

A content of such a compound (A) is preferably 1 to 80 parts by mass, more preferably 5 to 50 parts by mass, and particularly preferably 10 to 40 parts by mass, per 100 parts by mass of the ropinirole and/or the pharmaceutically acceptable salt thereof in terms of free ropinirole. If the content is below the lower limit, there is a tendency that the crystal formation cannot be suppressed sufficiently. On the other hand, if the content exceeds the upper limit, there is a tendency that the sufficient skin permeability of ropinirole cannot be kept.

Further, in the patch of the present invention, from viewpoint that the skin permeability of ropinirole is further improved, the adhesive agent layer 3 preferably further contains at least one compound selected from the group consisting of isopropyl myristate, isopropyl palmitate, lauryl alcohol, glycerol monooleate (GMO), propylene glycol monolaurate (PGML), polyoxyethylene sorbitan monooleate (Tween80), and lauric acid diethanolamide (LADA) (hereinafter sometimes referred to as compound (B)). Above all, it is particularly preferable to further contain isopropyl palmitate. The present inventors have found out that, in the patch of the present invention, when the adhesive agent layer 3 contains the compound (A) (particularly octyldodecanol), the skin permeability of ropinirole is reduced in some cases, and that by further incorporating the compound (B) (particularly isopropyl palmitate) in the adhesive agent layer 3, such a reduction in the skin permeability is suppressed, and the amount of ropinirole permeated through the skin is kept at quite a high level for a long period.

A content of such a compound (B) is preferably 5 to 200 parts by mass, more preferably 10 to 150 parts by mass, and particularly preferably 15 to 120 parts by mass, per 100 parts by mass of the ropinirole and/or the pharmaceutically acceptable salt thereof in terms of free ropinirole. If the content is below the lower limit, it tends to be difficult to achieve the effect of improving the skin permeability of ropinirole. On the other hand, even if the compound (B) is contained in an amount exceeding the upper limit, no further effect of improving the skin permeability is obtained; besides, the compound (B) exudes from the adhesive agent layer 3, so that the adhesion strength of the patch tends to be reduced.

In the present invention, the adhesive agent layer 3 further preferably contains the compound (A) and the compound (B), particularly preferably contains the octyldodecanol and the isopropyl palmitate, from the viewpoints that: the crystallization of the ropinirole free form is sufficiently suppressed, the skin permeability of ropinirole is further improved, and the amount of ropinirole permeated through the skin can be kept at quite a high level for a long period. A mixing ratio of the compound (A) with the compound (B) (compound (A) mass/compound (B) mass) is preferably 1/10 to 1/2. If the mixing ratio is below the lower limit, there is a tendency that the crystal formation of ropinirole cannot be suppressed sufficiently. On the other hand, if the mixing ratio exceeds the upper limit, there are tendencies that the skin permeability of ropinirole is reduced, and that a bleed occurs in the adhesive agent layer 3.

In the patch of the present invention, the adhesive agent layer 3 may further contain as necessary, in addition to the above compositions, a tackifier, a plasticizer, an absorption enhancer, an antioxidant, a filler, a preservative, an ultraviolet absorber, and the like, in such a range as not to inhibit the effects of the present invention.

Examples of the tackifier include rosin resins such as "Ester Gum (trade name, manufactured by Arakawa Chemical Industries, Ltd.)," "Hariester (trade name, manufactured by Harima Chemicals, Inc.)," "Pentalyn (trade name, manufactured by Eastman Chemical Company)," and "Foral (trade name, manufactured by Eastman Chemical Company)"; terpene resins such as "YS resin (trade name, manufactured by Yasuhara Chemical Co., Ltd.)" and "Piccolyte (trade name, manufactured by Loos and Dilworth Inc.)"; petroleum resins such as "Arkon (trade name, manufactured by Arakawa Chemical Industries, Ltd.)," "Regalrez (trade name, manufactured by Eastman Chemical Company)," "Piccolastic (trade name, manufactured by Eastman Chemical Company)," "Escorez (trade name, manufactured by ExxonMobil Chemical Company)," "Wingtack (trade name, manufactured by Goodyear Tire & Rubber Company)," and "Quintone (trade name, manufactured by Zeon Corporation)"; and alicyclic hydrocarbon resins such as phenolic resins and xylene resins. One of these may be used alone, or two or more thereof may be used in combination. When the adhesive agent layer 3 contains such a tackifier, a content thereof is preferably 10 to 80% by mass, more preferably 15 to 70% by mass, and further preferably 20 to 60% by mass, relative to the total mass of the adhesive agent layer 3, in consideration of the sufficient adhesion strength of the patch and the local irritation when the patch is released.

Examples of the plasticizer include petroleum oils such as paraffin process oils, naphthene process oils, and aromatic process oils; squalane and squalene; plant oils such as olive oil, camellia oil, castor oil, tall oil, and peanut oil; diprotic acid esters such as dibutyl phthalate and dioctyl phthalate; liquid rubbers such as polybutene and liquid isoprene rubber; diethylene glycol, polyethylene glycol, propylene glycol, dipropylene glycol, and the like. One of these may be used alone, or two or more thereof may be used in combination. The plasticizer is preferably liquid paraffin or liquid polybutene from the viewpoint that the adhesive agent layer 3 is provided with a preferable adhesion strength. When the adhesive agent layer 3 contains such a plasticizer, a content thereof is preferably 5 to 60% by mass, more preferably 5 to 50% by mass, and further preferably 7 to 40% by mass, relative to the total mass of the adhesive agent layer 3, in consideration of keeping a sufficient adhesion strength as the patch.

Examples of the absorption enhancer include, but excluding the compound (B), fatty alcohols such as isostearyl alcohol; fatty acids such as capric acid; fatty acid derivatives; polyethylene glycol, and the like. One of these may be used alone, or two or more thereof may be used in combination. When the adhesive agent layer 3 contains such an absorption enhancer, a content thereof excluding the content of the compound (B) is preferably 1 to 30% by mass, more preferably 3 to 20% by mass, and further preferably 5 to 15% by mass, relative to the total mass of the adhesive agent layer 3, in consideration of a sufficient permeability of the active ingredients to tissues, the local irritation, and the like as the preparation.

Examples of the antioxidant include tocopherols and ester derivatives thereof, ascorbic acid, ascorbyl stearate, nordihydroguaiaretic acid, dibutylhydroxytoluene (hereinafter abbreviated as BHT), butylated hydroxyanisole, and the like. One of these may be used alone, or two or more thereof may be used in combination.

Examples of the filler include aluminium hydroxide, calcium carbonate, magnesium carbonate; silicates such as aluminium silicate and magnesium silicate; silicic acid; barium sulfate, calcium sulfate; calcium zincate; zinc oxide, titanium oxide, and the like. Examples of the preservative include disodium edetate, tetrasodium edetate, ethyl parahydroxybenzoate, propyl parahydroxybenzoate, butyl parahydroxybenzoate, and the like. Examples of the ultraviolet absorber include p-aminobenzoic acid derivatives, anthranilic acid derivatives, salicylic acid derivatives, coumarin derivatives, amino acid compounds, imidazoline derivatives, pyrimidine derivatives, dioxane derivatives, and the like.

When the adhesive agent layer 3 contains the antioxidant, the filler, the preservative, and the ultraviolet absorber, a total content thereof is preferably 5% by mass or less, more preferably 3% by mass or less, and further preferably 1% by mass or less, relative to the total mass of the adhesive agent layer 3.

As to the thickness of the adhesive agent layer 3 according to the present invention, the thickness is preferably such that the adhesive agent layer 3 has a mass per unit area of 25 to 200 $g/m^2$, more preferably 25 to 180 $g/m^2$. If the thickness is below the lower limit, it tends to be difficult to keep the amount of ropinirole permeated through the skin in a sufficient amount. On the other hand, even if the thickness exceeds the upper limit, the sustainability of the amount of ropinirole permeated through the skin is not improved any more; in addition, the amount of the ropinirole and/or the pharmaceutically acceptable salt thereof required is also increased by the increased thickness, which tends to make the production cost comparatively expensive.

An area of an application surface per the ropinirole-containing patch of the present invention is preferably 0.5 to 100 $cm^2$. If the area is below the lower limit or exceeds the upper limit, it tends to be difficult to handle the patch.

Moreover, an application period of the ropinirole-containing patch of the present invention can be adjusted as appropriate. Nevertheless, the patch is preferably applied once in every 1 to 7 days.

Examples of a method for producing the ropinirole-containing patch of the present invention include: a method in which an adhesive agent layer composition obtained by mixing the adhesive base, the ropinirole and/or the pharmaceutically acceptable salt thereof, and as necessary other compositions described above in a solvent is spread directly on the support layer 2 to form the adhesive agent layer 3, and then the release sheet 4 for protecting the adhesive agent layer 3 is adhered on the adhesive agent layer 3; and a method in which the adhesive agent layer composition is spread on the release sheet 4 to form the adhesive agent layer 3, and the support layer 2 is placed thereon, followed by press-bonding transfer of the adhesive agent layer 3 onto the support layer 2.

The solvent is not particularly limited, and can be selected as appropriate, depending on ingredients to be dissolved or dispersed. Examples of the solvent include toluene, hexane, ethyl acetate, cyclohexane, heptane, butyl acetate, ethanol, methanol, xylene, isopropanol, and the like. One of these may be used alone, or two or more thereof may be used in combination.

A package of the present invention comprises the ropinirole-containing patch of the present invention and a deoxidizer together sealed in a packaging bag. From the viewpoints that the formation of ropinirole analogues can be further effectively suppressed and that the ropinirole stability over time is further improved, the patch of the present invention is preferably sealed in the packaging bag together with the deoxidizer during a period after the production until the time of the use. The packaging bag is not particularly limited, and one typically usable as a packaging bag of a patch can be used as appropriate. For example, it is preferably to use a plastic package, a plastic package with a metal layer (for example, an aluminium layer) formed, a metal package (for example, an aluminium package), or the like. Examples of the deoxidizer include those using iron powder and those containing vitamin C as the main ingredient. More specific examples include AGELESS series (manufactured by Mitsubishi Gas Chemical Company, Inc.), PharmaKeep series (manufactured by Mitsubishi Gas Chemical Company, Inc.), and the like.

The amount of the deoxidizer can be adjust as appropriate, depending on the mass of the patch, the material and volume of a container, and so forth. The deoxidizer preferably has such a mass that the amount of oxygen absorbed by the deoxidizer is 2.0 µl or larger.

EXAMPLES

Hereinafter, the present invention will be described more specifically based on Examples and Comparative Examples. However, the present invention is not limited to the following Examples. Note that, in each of Examples and Comparative Examples, a skin permeation test, an evaluation test for stability over time, an evaluation test for aggregation in the adhesive agent layer, an evaluation test for adhesiveness, and an evaluation test for storing stability were respectively conducted according to methods described below.

(Skin Permeation Test (In Vitro))

First, the dorsal skin of a hairless mouse was extirpated and mounted on a Franz flow-through cell in such a manner that the dermal side was placed on the receptor side, warm water of 32° C. being circulated around the outer portion of the cell. Then, a patch immediately after the production (within 72 hours after the production) which had been cut to a size of 5 cm$^2$, and from which the release sheet had been removed, was applied to the stratum corneum side of the skin. Phosphate buffered saline (PBS) having a pH of 7.4 was caused to flow at a constant flow volume through the receptor of the flow-through cell, and sample solutions were collected from the receptor every two hours for 24 hours. The concentration of a drug (ropinirole) in each of the sample solutions thus collected was quantitated by high-performance liquid chromatography to obtain the amount of the drug permeated the skin for each period. The maximum permeation rate (Flux: µg/cm$^2$/hr) of the drug was calculated according to the following formula:

Flux (µg/cm$^2$/hr)=[drug concentration (µg/ml)×flow volume (ml)]/patch area (cm$^2$)/time (hr).

Moreover, a ratio (utilization ratio: %) of a total mass of the drug permeated for 24 hours after the measurement was started (cumulative permeated amount) to a mass of the drug contained when the was patch was produced (initial amount) was calculated according to the following formula:

Utilization ratio (%)=[cumulative permeated amount (µg/cm$^2$)/initial amount (µg/cm$^2$)]×100.

A preparation having larger values of the maximum permeation rate and the utilization ratio can be recognized as having an excellent skin permeability of the drug.

Further, the maximum permeation rate (Flux) and the utilization ratio of a patch was calculated in the same manner as described above, except that the patch used had been alone or together with a deoxidizer (Ageless ZJ-15PT, manufactured by Mitsubishi Gas Chemical Company, Inc.) packaged and sealed in a packaging bag made of cellonium, and then left standing and stored at 60° C. for 2 weeks (for 14 days).

(Evaluation Test for Stability Over Time)

A sample of 6.25 cm$^2$ was collected from a patch immediately after the production (within 72 hours after the production), and 10 ml of tetrahydrofuran was added thereto to dissolve the adhesive agent layer. To this solution, a 50% methanol aqueous solution was added a total amount of 50 ml. Then, a measurement sample was obtained by filter filtration. Contents (% by mass) of ropinirole and unknown compounds (ropinirole analogues) in the obtained measurement sample were measured using a high-performance liquid chromatograph (manufactured by Shimadzu Corporation, column: ODS column, mobile phase: 10 mM sodium nonane-sulfonate-2% phosphoric acid aqueous solution/methanol (50/50 (volume ratio)), detection wavelength: 250 nm). Moreover, the amount of the drug remained (%) was calculated according to the following formula:

Amount of drug remained (%)=ropinirole content/ [ropinirole content+total content of ropinirole analogues]×100.

Further, the amount of the drug remained in a patch was calculated by the same measurement described above, except that the patch used had been alone or together with a deoxidizer (Ageless ZJ-15PT, manufactured by Mitsubishi Gas Chemical Company, Inc.) packaged and sealed in a packaging bag made of cellonium, and then left standing and stored at 60° C. for 2 weeks (for 14 days).

(Evaluation Test for Aggregation in Adhesive Agent Layer)

The surface of an adhesive agent layer of a patch from which the release sheet had been removed was strongly pressed with a finger. When the two were separated, the amount of the adhesive base remained on the finger was visually observed and evaluated according to the following criteria:

A: no adhesive base remained, exhibiting a favorable aggregation ability

B: only a slight amount of the adhesive base remained, exhibiting an aggregation ability C: a large amount of the adhesive base remained, exhibiting a weak aggregation ability.

(Evaluation Test for Adhesiveness of Adhesive Agent Layer)

A release sheet was removed from a patch immediately after the production (after the production within 72 hours), and a tack value (gF) was measured using a tackiness tester (TAC-2, manufactured by RHESCA Corporation) under conditions: a contact period of 1 sec with a stainless probe, and a measurement speed of 5 mm/sec. A preparation having a larger tack value can be recognized as having an excellent adhesiveness.

Further, the tack value of a patch was measured in the same manner as described above, except that the patch used had been alone or together with a deoxidizer (Ageless ZJ-15PT, manufactured by Mitsubishi Gas Chemical Company, Inc.) packaged and sealed in a packaging bag made of cellonium, and then left standing and stored at 60° C. for 2 weeks (for 14 days).

(Evaluation Test for Storing Stability)

A patch was packaged and sealed in a packaging bag together with a deoxidizer, and then left standing and stored at 4° C. for 30 days. After the storage for 30 days, the adhesive agent layer of the patch was observed visually and under a microscope, and evaluated according to the following criteria:

A: no crystal formation was observed on the adhesive agent layer

B: radiating acicular crystals were observed on partial or entire surface of the adhesive agent layer.

Example 1

First, using a mixer, 10.0 parts by mass of ropinirole hydrochloride (8.8 parts by mass in terms of free ropinirole), 1.1 parts by mass of sodium hydroxide (desalting agent), 29.6 parts by mass of liquid paraffin, toluene (solvent), 29.6 parts by mass of a styrene-isoprene-styrene block copolymer (SIS) (SIS5000, manufactured by JSR Corporation), and 29.6 parts by mass of an alicyclic hydrocarbon resin were mixed to obtain an adhesive agent layer composition. The obtained adhesive agent layer composition was spread on a release sheet formed from a film (made of polyester) release-treated with a silicone, and dried to remove toluene, thereby forming an adhesive agent layer. Then, a film (made of polyester) to serve as a support layer was laminated on the opposite surface of the adhesive agent layer from the release sheet, and a patch was thus obtained. Table 1 shows the composition of the adhesive agent layer composition (excluding toluene). Note that, in the obtained patch, the adhesive agent layer had such a thickness that the adhesive agent layer had a mass per unit area of 100 g/m$^2$.

Example 2, Comparative Examples 1 and 2

Figure 2:
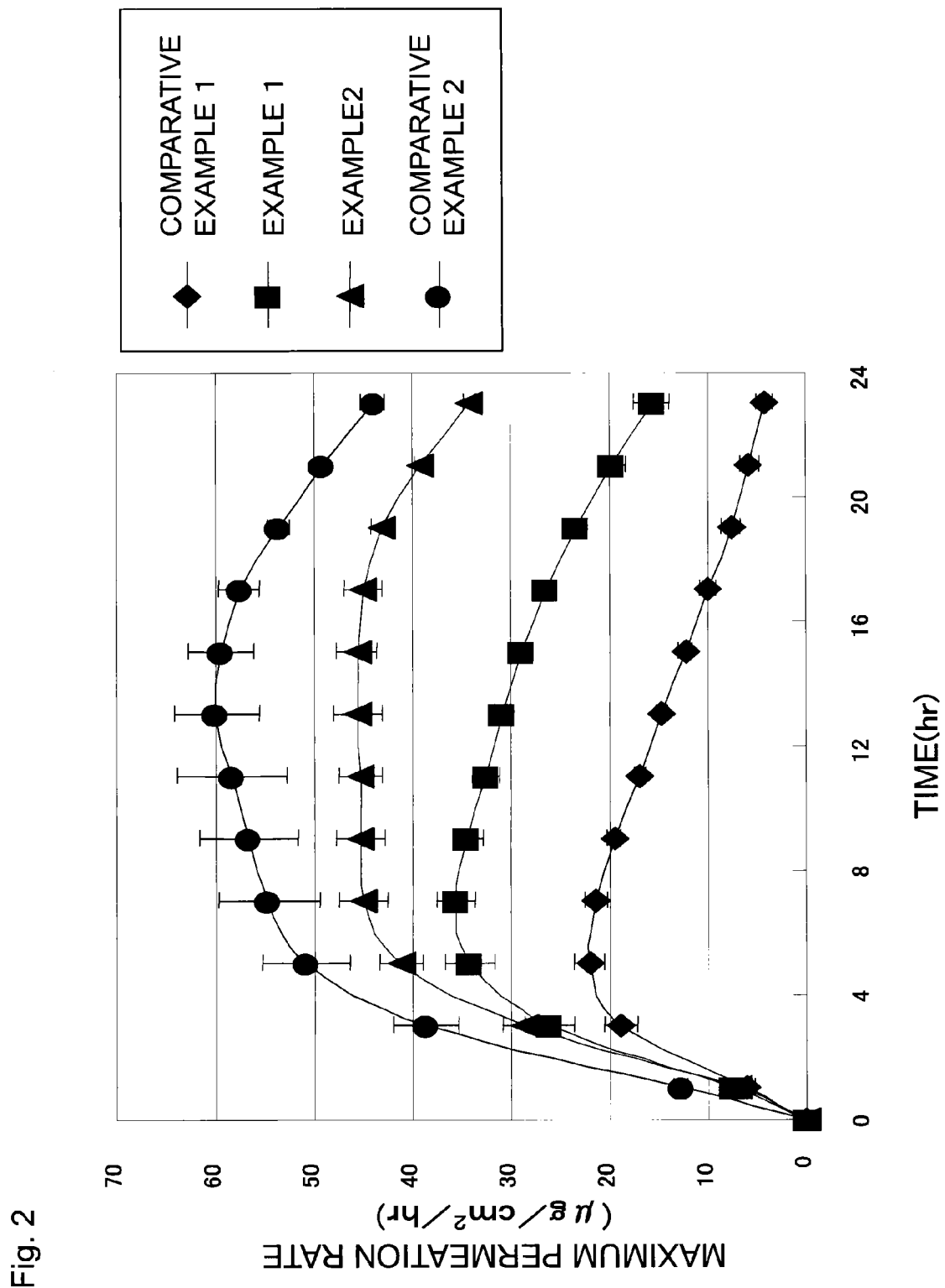
FIG. 2 is a graph showing the result of conducting a skin permeation test on patches obtained in Examples 1 to 2 and Comparative Examples 1 to 2.

Patches were obtained in the same manner as in Example 1, except that the adhesive agent layer compositions had compositions shown in Table 1. Each of the patches obtained in Examples 1 and 2 as well as Comparative Examples 1 and 2 was subjected to the skin permeation test and the evaluation test for aggregation in the adhesive agent layer. Table 1 shows the result of the evaluation test for aggregation in the adhesive agent layer together with the composition of the adhesive agent layer composition in each Example and Comparative Example. FIG. 2 shows the result of the skin permeation test.

TABLE 1

| Composition of adhesive agent layer composition (parts by mass) | Example 1 | Example 2 | Comparative Example 1 | Comparative Example 2 |
|---|---|---|---|---|
| SIS | 29.6 | 27.8 | 31.5 | 25.9 |
| alicyclic hydrocarbon resin | 29.6 | 27.8 | 31.5 | 25.9 |
| liquid paraffin | 29.6 | 27.8 | 31.5 | 25.9 |
| ropinirole hydrochloride | 10.0 | 15.0 | 5.0 | 20.0 |
| (parts by mass in terms of free ropinirole) | (8.8) | (13.2) | (4.4) | (17.5) |
| sodium hydroxide | 1.1 | 1.6 | 0.5 | 2.2 |
| aggregation evaluation | A | B | A | C |

As apparent from the results shown in Table 1 and FIG. 2, it was verified that the patch of the present invention had an excellent skin permeability of ropinirole and a strong aggregation ability of the adhesive agent layer and was capable of demonstrating a sufficient adhesiveness. In contrast, it was verified that the patch having a low content of ropinirole and/or a pharmaceutically acceptable salt thereof (Comparative Example 1) had a small amount of ropinirole permeated the skin and was not capable of keeping the amount of ropinirole permeated through the skin sufficiently for a long period. Further, it was verified that: the patch having a high content of ropinirole and/or a pharmaceutically acceptable salt thereof (Comparative Example 2) had a weak aggregation ability of the adhesive agent layer, the applicability was quite poor, and the use thereof as a patch was difficult.

Example 3

A patch was obtained in the same manner as in Example 1, except that the adhesive agent layer composition had a composition shown in Table 2.

Example 4

A patch was obtained in the same manner as in Example 1, except that the adhesive agent layer composition had a composition shown in Table 2, and that 5.0 parts by mass of isopropyl myristate was further added.

Example 5

A patch was obtained in the same manner as in Example 1, except that the adhesive agent layer composition had a composition shown in Table 2, and that 5.0 parts by mass of isopropyl palmitate was further added.

Example 6

A patch was obtained in the same manner as in Example 1, except that the adhesive agent layer composition had a composition shown in Table 2, and that 5.0 parts by mass of octyldodecanol was further added.

Example 7

A patch was obtained in the same manner as in Example 1, except that the adhesive agent layer composition had a composition shown in Table 2, and that 5.0 parts by mass of lauryl alcohol was further added.

Example 8

A patch was obtained in the same manner as in Example 1, except that the adhesive agent layer composition had a composition shown in Table 2, and that 5.0 parts by mass of oleyl alcohol was further added.

Example 9

A patch was obtained in the same manner as in Example 1, except that the adhesive agent layer composition had a composition shown in Table 2, and that 5.0 parts by mass of glycerol monooleate (GMO) was further added.

Example 10

A patch was obtained in the same manner as in Example 1, except that the adhesive agent layer composition had a composition shown in Table 2, and that 5.0 parts by mass of propylene glycol monolaurate (PGML) was further added.

Example 11

A patch was obtained in the same manner as in Example 1, except that the adhesive agent layer composition had a composition shown in Table 2, and that 5.0 parts by mass of polyoxyethylene sorbitan monooleate (Tween80) was further added.

Example 12

A patch was obtained in the same manner as in Example 1, except that the adhesive agent layer composition had a composition shown in Table 2, and that 5.0 parts by mass of lauric acid diethanolamide (LADA) was further added.

Figure 3:
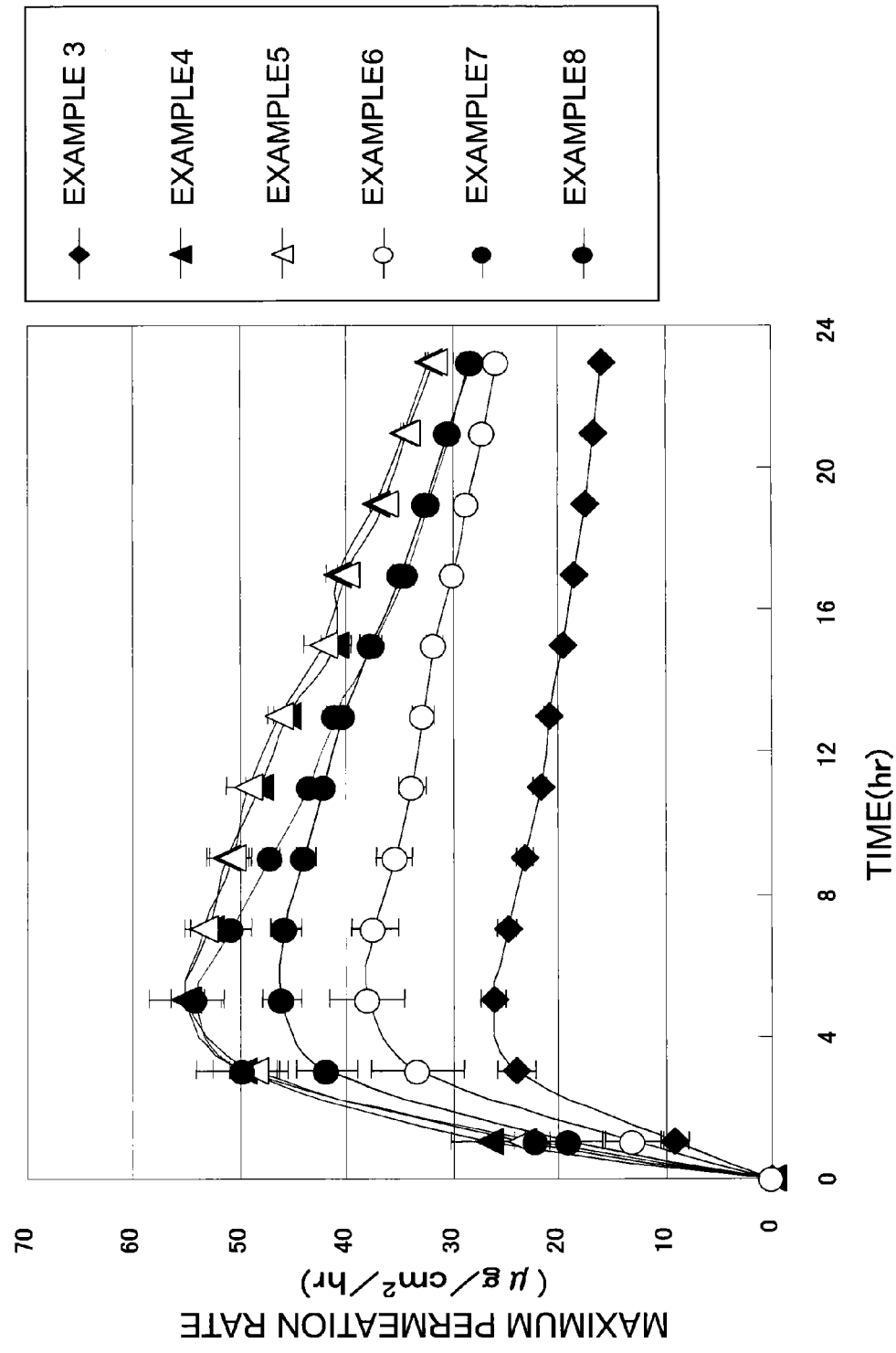
FIG. 3 is a graph showing the result of conducting the skin permeation test on patches obtained in Examples 3 to 8.

Table 2 shows the compositions of the adhesive agent layer compositions of the patches obtained in Examples 3 to 12. Moreover, each of the patches obtained in Examples 3 to 12 was subjected to the skin permeation test. FIG. 3 shows the result obtained in Examples 3 to 8, and FIG. 4 shows the result obtained in Examples 3 and 9 to 12.

TABLE 2

| Composition of adhesive agent layer composition (parts by mass) | Example 3 | Example 4 | Example 5 | Example 6 | Example 7 | Example 8 | Example 9 | Example 10 | Example 11 | Example 12 |
|---|---|---|---|---|---|---|---|---|---|---|
| SIS | 13.9 | 13.1 | 13.1 | 13.1 | 13.1 | 13.1 | 13.1 | 13.1 | 13.1 | 13.1 |
| PIB | 13.9 | 13.1 | 13.1 | 13.1 | 13.1 | 13.1 | 13.1 | 13.1 | 13.1 | 13.1 |
| alicyclic hydrocarbon resin | 41.7 | 39.2 | 39.2 | 39.2 | 39.2 | 39.2 | 39.2 | 39.2 | 39.2 | 39.2 |
| liquid paraffin | 13.9 | 13.1 | 13.1 | 13.1 | 13.1 | 13.1 | 13.1 | 13.1 | 13.1 | 13.1 |
| ropinirole hydrochloride | 15.0 | 15.0 | 15.0 | 15.0 | 15.0 | 15.0 | 15.0 | 15.0 | 15.0 | 15.0 |
| (parts by mass in terms of free ropinirole) | (13.2) | (13.2) | (13.2) | (13.2) | (13.2) | (13.2) | (13.2) | (13.2) | (13.2) | (13.2) |
| added compound — compound name | — | isopropyl myristate | isopropyl palmitate | octyl dodecanol | lauryl alcohol | oleyl alcohol | GMO | PGML | Tween 80 | LADA |
| parts by mass | — | 5.0 | 5.0 | 5.0 | 5.0 | 5.0 | 5.0 | 5.0 | 5.0 | 5.0 |
| parts by mass per 100 parts by mass of free ropinirole | — | 37.9 | 37.9 | 37.9 | 37.9 | 37.9 | 37.9 | 37.9 | 37.9 | 37.9 |
| sodium hydroxide | 1.6 | 1.6 | 1.6 | 1.6 | 1.6 | 1.6 | 1.6 | 1.6 | 1.6 | 1.6 |

Figure 4:
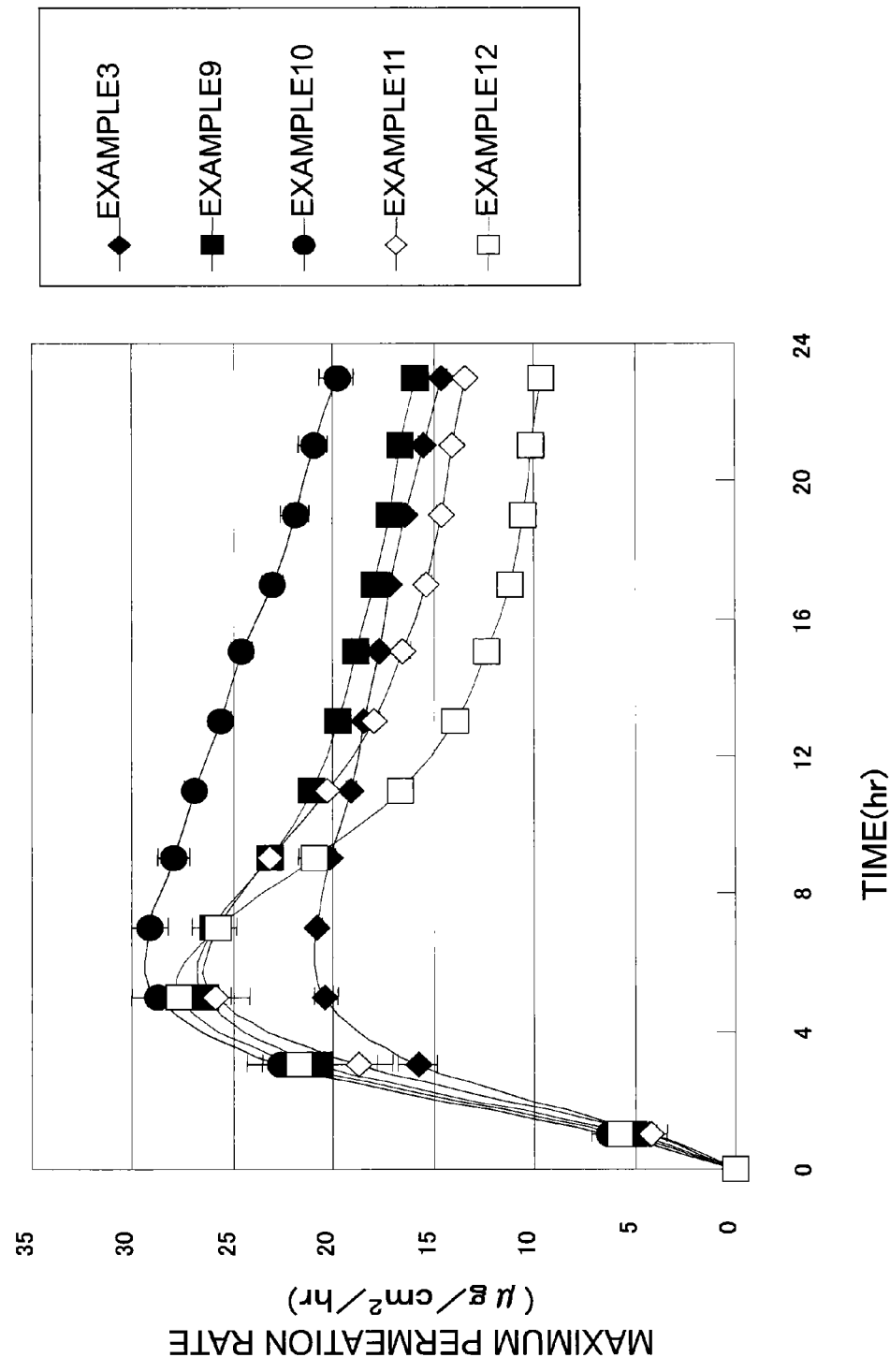
FIG. 4 is a graph showing the result of conducting the skin permeation test on patches obtained in Examples 3 and 9 to 12.

As apparent from the results shown in FIGS. 3 and 4, it was verified that the patch of the present invention had an excellent skin permeability of ropinirole. It was verified that this effect was still achieved or was further improved even when any compound of isopropyl myristate, isopropyl palmitate, lauryl alcohol, glycerol monooleate, propylene glycol monolaurate, polyoxyethylene sorbitan monooleate, and lauric acid diethanolamide was further used in combination.

Examples 13 to 19

Patches were obtained in the same manner as in Example 5, except that the adhesive agent layer compositions respectively had compositions shown in Table 3. Table 3 shows the compositions of the adhesive agent layer compositions of the patches obtained in Examples 13 to 19. Moreover, FIG. 5 shows the result of conducting the skin permeation test on each of the patches obtained in Examples 13 to 19.

TABLE 3

| Composition of adhesive agent layer composition | Example 13 | Example 14 | Example 15 | Example 16 | Example 17 | Example 18 | Example 19 |
|---|---|---|---|---|---|---|---|
| SIS | 4.8 | 4.6 | 4.5 | 4.3 | 4.2 | 4.1 | 3.9 |
| PIB | 19.1 | 18.5 | 17.9 | 17.3 | 16.8 | 16.2 | 15.6 |
| alicyclic hydrocarbon resin | 35.7 | 34.7 | 33.6 | 32.5 | 31.4 | 30.4 | 29.3 |
| liquid paraffin | 23.8 | 23.1 | 22.4 | 21.7 | 21.0 | 20.3 | 19.5 |
| ropinirole hydrochloride | 15.0 | 15.0 | 15.0 | 15.0 | 15.0 | 15.0 | 15.0 |
| (parts by mass in terms of free ropinirole) | (13.2) | (13.2) | (13.2) | (13.2) | (13.2) | (13.2) | (13.2) |
| isopropyl palmitate — parts by mass | — | 2.5 | 5.0 | 7.5 | 10.0 | 12.5 | 15.0 |
| parts by mass per 100 parts by mass of free ropinirole | — | 18.9 | 37.9 | 56.8 | 75.8 | 94.7 | 113.6 |
| sodium hydroxide | 1.6 | 1.6 | 1.6 | 1.6 | 1.6 | 1.6 | 1.6 |

Figure 5:
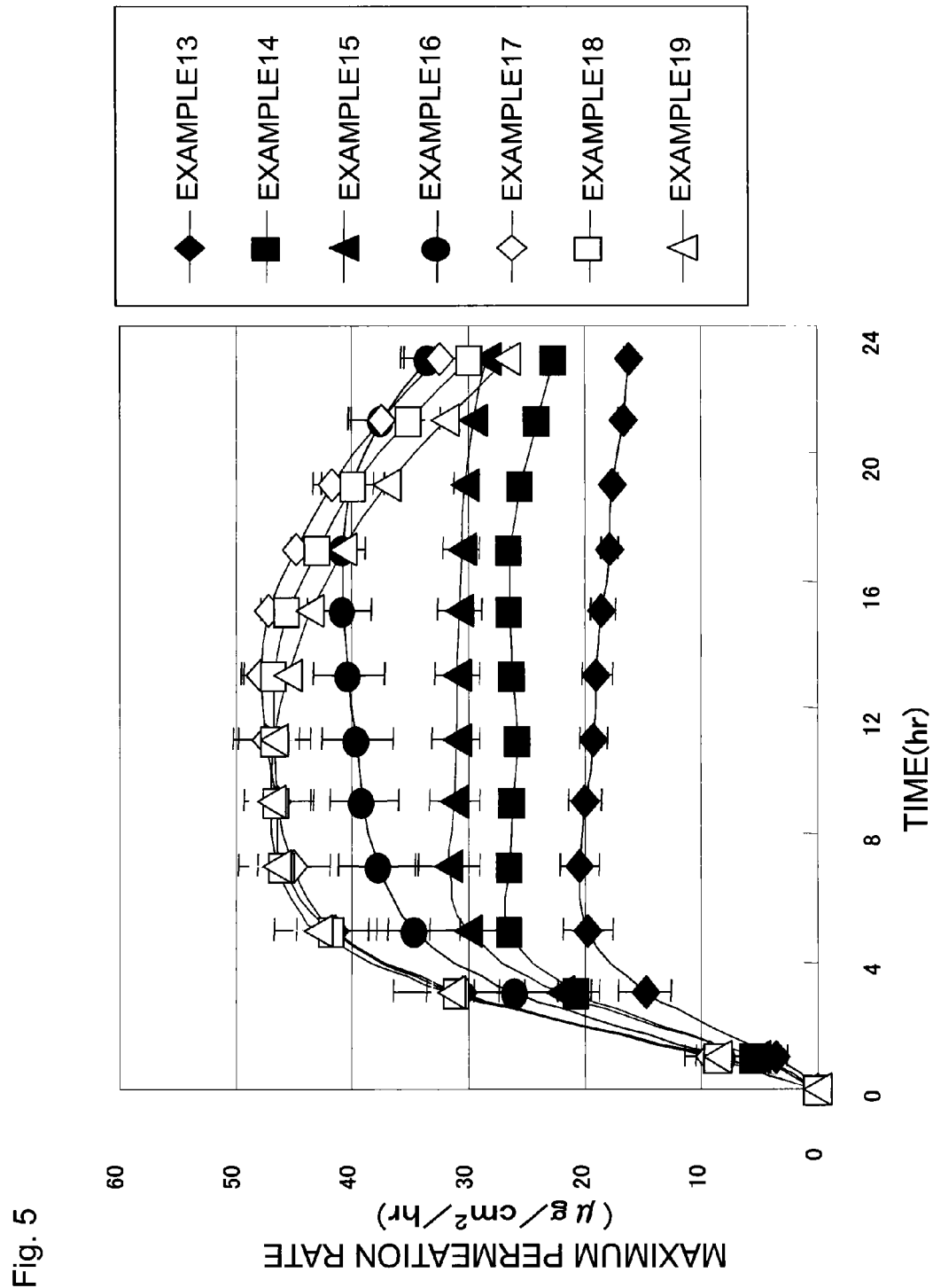
FIG. 5 is a graph showing the result of conducting the skin permeation test on patches obtained in Examples 13 to 19.

As apparent from the result shown in FIG. 5, it was verified that the patch of the present invention had an excellent skin permeability of ropinirole. When isopropyl palmitate was further used in combination, this effect was increased as the concentration of isopropyl palmitate was increased until the concentration reached a certain value.

Example 20

A patch was obtained in the same manner as in Example 5, except that the adhesive agent layer composition had a composition shown in Table 4.

Example 21

A patch was obtained in the same manner as in Example 20, except that the adhesive agent layer composition had a composition shown in Table 4, and that 5.0 parts by mass of benzyl alcohol was further added.

Example 22

A patch was obtained in the same manner as in Example 20, except that the adhesive agent layer composition had a composition shown in Table 4, and that 5.0 parts by mass of oleyl alcohol was further added.

Example 23

A patch was obtained in the same manner as in Example 20, except that the adhesive agent layer composition had a composition shown in Table 4, and that 5.0 parts by mass of octyldodecanol was further added.

Example 24

A patch was obtained in the same manner as in Example 20, except that the adhesive agent layer composition had a composition shown in Table 4, and that 5.0 parts by mass of dimethyl isosorbide was further added.

Examples 25 to 29

Patches were obtained in the same manner as in Example 23, except that the adhesive agent layer compositions respectively had compositions shown in Table 4.

Figure 6:
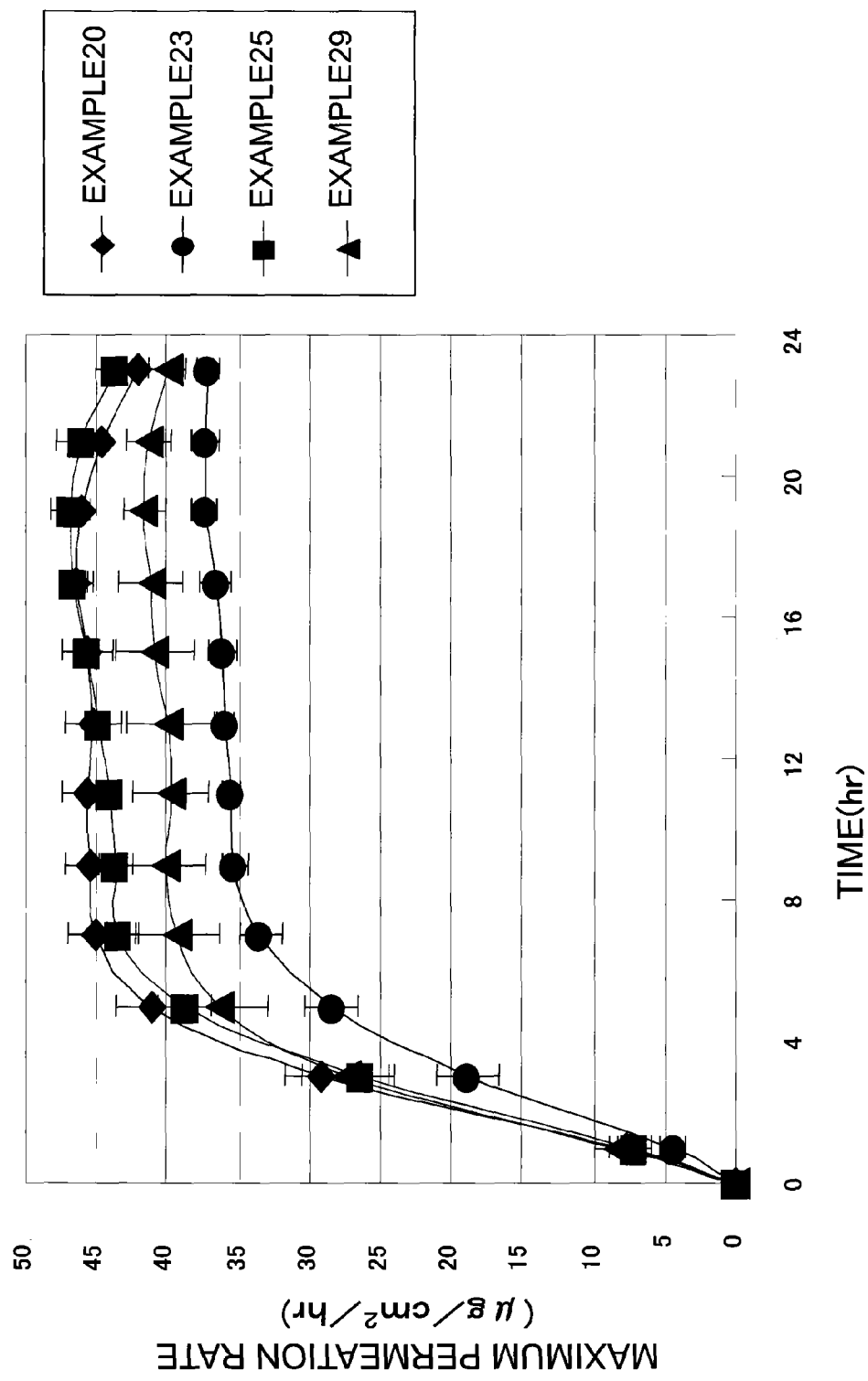
FIG. 6 is a graph showing the result of conducting the skin permeation test on patches obtained in Examples 20, 23, 25, and 29.

Each of the patches obtained in Examples 20 to 29 was subjected to the skin permeation test and the evaluation test for storing stability. Table 4 shows the result of the evaluation test for storing stability together with the composition of the adhesive agent layer composition in each Example. Moreover, FIG. 6 shows the result of conducting the skin permeation test on each of the patches obtained in Examples 20, 23, 25, and 29.

palmitate and a specific content of any compound of benzyl alcohol, oleyl alcohol, octyldodecanol, and dimethyl isosorbide had an excellent skin permeability of ropinirole, suppressed over time formation of crystals from the ropinirole free form even when stored for a long period, and was capable of keeping the amount of ropinirole permeated through the skin at quite a high level for a long period.

Examples 30 and 31, Comparative Examples 3 and 4

Patches were obtained in the same manner as in Example 1, except that the adhesive agent layer compositions had compositions shown in Table 5. Each of the patches obtained in Examples 30 and 31 as well as Comparative Examples 3 and 4 was subjected to the skin permeation test, the evaluation test for stability over time, and the evaluation test for adhesive-

TABLE 4

| Composition of adhesive agent layer composition (parts by mass) | Example 20 | Example 21 | Example 22 | Example 23 | Example 24 | Example 25 | Example 26 | Example 27 | Example 28 | Example 29 |
|---|---|---|---|---|---|---|---|---|---|---|
| SIS | 15.7 | 15.7 | 15.7 | 15.7 | 15.7 | 15.0 | 14.9 | 14.8 | 14.7 | 14.6 |
| PIB | — | — | — | — | — | 3.8 | 3.7 | 3.7 | 3.7 | 3.7 |
| alicyclic hydrocarbon resin | 47.0 | 47.0 | 47.0 | 47.0 | 47.0 | 47.0 | 46.6 | 46.3 | 46.0 | 45.6 |
| liquid paraffin | 16.3 | 11.3 | 11.3 | 11.3 | 11.3 | 12.2 | 12.3 | 12.2 | 12.1 | 12.1 |
| ropinirole hydrochloride | 15.0 | 15.0 | 15.0 | 15.0 | 15.0 | 15.0 | 15.0 | 15.0 | 15.0 | 15.0 |
| (parts by mass in terms of free ropinirole) | (13.2) | (13.2) | (13.2) | (13.2) | (13.2) | (13.2) | (13.2) | (13.2) | (13.2) | (13.2) |
| isopropyl palmitate | 10.0 | 10.0 | 10.0 | 10.0 | 10.0 | 10.0 | 10.0 | 10.0 | 10.0 | 10.0 |
| (parts by mass per 100 parts by mass of free ropinirole) | (75.8) | (75.8) | (75.8) | (75.8) | (75.8) | (75.8) | (75.8) | (75.8) | (75.8) | (75.8) |
| benzyl alcohol | — | 5.0 | — | — | — | — | — | — | — | — |
| (parts by mass per 100 parts by mass of free ropinirole) | | (37.9) | | | | | | | | |
| oleyl alcohol | — | — | 5.0 | — | — | — | — | — | — | — |
| (parts by mass per 100 parts by mass of free ropinirole) | | | (37.9) | | | | | | | |
| octyldodecanol | — | — | — | 5.0 | — | 1.0 | 1.5 | 2.0 | 2.5 | 3.0 |
| (parts by mass per 100 parts by mass of free ropinirole) | | | | (37.9) | | (7.5) | (11.4) | (15.2) | (18.9) | (22.7) |
| dimethyl isosorbide | — | — | — | — | 5.0 | — | — | — | — | — |
| (parts by mass per 100 parts by mass of free ropinirole) | | | | | (37.9) | | | | | |
| storing stability evaluation | B | A | A | A | A | B | B | B | A | A |

As apparent from the results shown in Table 4 and FIG. 6, it was verified that even when stored for a long period, the patch of the present invention comprising the adhesive agent layer further containing a specific content of any compound of benzyl alcohol, oleyl alcohol, octyldodecanol, and dimethyl isosorbide suppressed over time formation of crystals from the ropinirole free form. Further, it was verified that the patch of the present invention further containing isopropyl ness of the adhesive agent layer. Table 5 shows the utilization ratio and the maximum permeation rate for 24 hours after the measurement was started, which were obtained in the skin permeation test, and the tack value obtained in the evaluation test for adhesiveness of the adhesive agent layer, together with the composition of the adhesive agent layer composition in each Example and Comparative Example. Table 6 shows the result of the evaluation test for stability over time.

TABLE 5

| Composition of adhesive agent layer composition (parts by mass) | | Example 30 | Example 31 | Comparative Example 3 | Comparative Example 4 |
|---|---|---|---|---|---|
| SIS | | 25.4 | 23.8 | 27.0 | 22.2 |
| alicyclic hydrocarbon resin | | 43.2 | 40.5 | 45.9 | 37.8 |
| liquid paraffin | | 20.3 | 19.1 | 21.6 | 17.8 |
| ropinirole hydrochloride | | 10.0 | 15.0 | 5.0 | 20.0 |
| (parts by mass in terms of free ropinirole) | | (8.8) | (13.2) | (4.4) | (17.5) |
| sodium hydroxide | | 1.1 | 1.6 | 0.5 | 2.2 |
| maximum permeation | immediately after production | 18.6 | 22.5 | 11.4 | 26.0 |

TABLE 5-continued

| Composition of adhesive agent layer composition (parts by mass) | | Example 30 | Example 31 | Comparative Example 3 | Comparative Example 4 |
|---|---|---|---|---|---|
| rate ($\mu g/cm^2/hr$) | 60° C., after 2-week storage (with deoxidizer) | 17.0 | 21.1 | 11.7 | 23.8 |
| utilization ratio (%) | immediately after production | 35.2 | 28.4 | 42.1 | 25.7 |
| | 60° C., after 2-week storage (with deoxidizer) | 32.6 | 27.1 | 43.3 | 23.6 |
| tack value (gF) | immediately after production | 333 | 320 | 356 | 164 |
| | 60° C., after 2-week storage (with deoxidizer) | 350 | 348 | 348 | 234 |

TABLE 6

| | | content (mass %) | | | | | | | | | | | | amount of drug remained (%) |
|---|---|---|---|---|---|---|---|---|---|---|---|---|---|---|
| | | | unknown compound | | | | | | | | | | | |
| | | | column retention time (hr) | | | | | | | | | | | |
| | | ropinirole | 4.4 | 6.1 | 7.0 | 7.4 | 7.7 | 8.0 | 8.4 | 10.4 | 18.9 | 24.0 | total | |
| Example 30 | immediately after production | 102.3 | — | tr | tr | — | 0.17 | — | — | tr | — | — | 0.17 | — |
| | 60° C., after 2-week storage (without deoxidizer) | 94.4 | 0.10 | — | — | 0.14 | — | 0.25 | — | 3.75 | — | 0.73 | 4.97 | 92.3 |
| | 60° C., after 2-week storage (with deoxidizer) | 101.0 | tr | — | — | — | — | — | tr | 0.16 | — | — | 0.16 | 98.7 |
| Example 31 | immediately after production | 100.5 | — | tr | tr | — | 0.10 | — | tr | 0.05 | — | — | 0.15 | — |
| | 60° C., after 2-week storage (without deoxidizer) | 82.6 | 0.39 | 0.05 | 0.08 | 0.13 | 0.10 | 0.14 | — | 4.02 | 0.14 | 0.07 | 5.12 | 82.2 |
| | 60° C., after 2-week storage (with deoxidizer) | 98.5 | tr | — | — | tr | — | tr | — | 0.12 | — | — | 0.12 | 98.0 |
| Comparative Example 3 | immediately after production | 102.9 | — | — | — | tr | — | — | — | — | — | — | 0.00 | — |
| | 60° C., after 2-week storage (without deoxidizer) | 98.6 | tr | tr | tr | 0.10 | — | 0.20 | — | 2.24 | — | 0.10 | 2.64 | 95.8 |
| | 60° C., after 2-week storage (with deoxidizer) | 101.4 | tr | — | — | 0.22 | — | — | — | 0.18 | — | — | 0.40 | 98.5 |
| Comparative Example 4 | immediately after production | 101.4 | — | 0.05 | tr | tr | tr | tr | tr | 0.11 | tr | — | 0.16 | — |
| | 60° C., after 2-week storage (without deoxidizer) | 79.7 | 0.58 | 0.20 | 0.09 | 0.09 | 0.08 | 0.08 | — | 3.24 | 0.22 | 0.07 | 4.65 | 78.6 |
| | 60° C., after 2-week storage (with deoxidizer) | 99.3 | 0.01 | — | — | — | tr | — | tr | 0.12 | — | tr | 0.13 | 97.9 |

In Table 6, "tr" indicates that the detected amount was too small to be represented by a numerical value As apparent from the results shown in Tables 5 and 6, it was verified that the patch of the present invention had excellent skin permeability of ropinirole and ropinirole stability over time and was capable of demonstrating a sufficient adhesiveness. Further, it was verified that a higher content of ropinirole and/or a pharmaceutically acceptable salt thereof improved the skin permeability of ropinirole, but reduced the stability over time and the adhesiveness. Furthermore, it was verified that by packaging and storing the patch of the present invention together with the deoxidizer, the ropinirole stability over time was further improved.

Comparative Examples 5 to 16

Patches were obtained in the same manner as in Example 1, except that the adhesive agent layer compositions had compositions shown in Table 7. Each of the patches obtained in Comparative Examples 5 to 16 was subjected to the skin permeation test and the evaluation test for stability over time. Table 8 shows the maximum permeation rate for 24 hours after the measurement was started, which was obtain in the skin permeation test, and the result of the evaluation test for stability over time.

TABLE 7

| Composition of adhesive agent layer composition (parts by mass) | | Comparative Example 5 | Comparative Example 6 | Comparative Example 7 | Comparative Example 8 | Comparative Example 9 | Comparative Example 10 | Comparative Example 11 |
|---|---|---|---|---|---|---|---|---|
| SIS | | 24.7 | — | — | — | 23.7 | — | — |
| alicyclic hydrocarbon resin | | 41.2 | — | — | — | 39.4 | — | — |
| liquid paraffin | | 29.1 | — | — | — | 27.8 | — | — |
| ropinirole hydrochloride | | 5.0 | 5.0 | 5.0 | 5.0 | 5.0 | 5.0 | 5.0 |
| (parts by mass in terms of free ropinirole) | | (4.4) | (4.4) | (4.4) | (4.4) | (4.4) | (4.4) | (4.4) |
| acrylic-based adhesive | Duro-Tak 87-2516 (OH group containing type) | — | 95.0 | — | — | — | 90.9 | — |
| | Duro-Tak 87-2194 (COOH group containing type) | — | — | 95.0 | — | — | — | 90.9 |
| | Duro-Tak 87-900A (no functional group type) | — | — | — | 95.0 | — | — | — |
| sodium acetate | | — | — | — | — | 4.1 | 4.1 | 4.1 |
| sodium hydroxide | | — | — | — | — | — | — | — |

| Composition of adhesive agent layer composition (parts by mass) | | Comparative Example 12 | Comparative Example 13 | Comparative Example 14 | Comparative Example 15 | Comparative Example 16 |
|---|---|---|---|---|---|---|
| SIS | | — | 24.6 | — | — | — |
| alicyclic hydrocarbon resin | | — | 40.8 | — | — | — |
| liquid paraffin | | — | 28.9 | — | — | — |
| ropinirole hydrochloride | | 5.0 | 5.0 | 5.0 | 5.0 | 5.0 |
| (parts by mass in terms of free ropinirole) | | (4.4) | (4.4) | (4.4) | (4.4) | (4.4) |
| acrylic-based adhesive | Duro-Tak 87-2516 (OH group containing type) | — | — | 94.3 | — | — |
| | Duro-Tak 87-2194 (COOH group containing type) | — | — | — | 94.3 | — |
| | Duro-Tak 87-900A (no functional group type) | 90.9 | — | — | — | 94.3 |
| sodium acetate | | 4.1 | — | — | — | — |
| sodium hydroxide | | — | 0.7 | 0.7 | 0.7 | 0.7 |

TABLE 8

| | maximum permeation rate (μg/cm²/hr) | content (mass %) | | | | | | | | | | | | | amount of drug remained (%) |
|---|---|---|---|---|---|---|---|---|---|---|---|---|---|---|---|
| | | ropinirole | unknown compound | | | | | | | | | | | | |
| | | | column retention time (hr) | | | | | | | | | | | | |
| | | | 3.3 | 3.8 | 4.2 | 5.7 | 6.1 | 7.5 | 7.8 | 8.2 | 9.0 | 9.9 | 10.2 | 18.6 | total | |
| Comparative Example 5 | 0.34 | 99.4 | — | — | — | — | — | — | — | — | — | — | — | — | 0.00 | 100.0 |
| Comparative Example 6 | 0.52 | 96.3 | — | — | — | — | — | 0.06 | — | — | — | — | — | — | 0.06 | 99.9 |
| Comparative Example 7 | 0.44 | 95.7 | 3.01 | 0.15 | — | — | — | — | — | — | 0.08 | — | — | — | 3.24 | 96.8 |
| Comparative Example 8 | 0.94 | 97.3 | — | — | — | — | — | — | — | — | — | — | — | 0.41 | 0.41 | 99.6 |
| Comparative Example 9 | 0.96 | 96.6 | — | — | — | — | — | — | — | — | — | — | — | — | 0.00 | 100.0 |
| Comparative Example 10 | >5.47 | 90.1 | 1.53 | 0.05 | 0.06 | 0.09 | 0.15 | 2.78 | 0.28 | 0.06 | — | — | 4.43 | — | 9.43 | 90.2 |
| Comparative Example 11 | >0.68 | 89.4 | 0.82 | 0.16 | — | 0.96 | 0.16 | 7.39 | — | — | 0.12 | 1.10 | 0.20 | — | 10.91 | 89.1 |
| Comparative Example 12 | >3.30 | 102.6 | 0.97 | 0.06 | tr | — | — | 0.36 | 0.10 | 0.08 | — | — | 2.40 | 0.40 | 4.37 | 95.9 |
| Comparative Example 13 | 13.73 | 99.0 | — | — | — | — | — | — | — | — | — | — | — | — | 0.00 | 100.0 |
| Comparative Example 14 | >5.37 | 97.6 | 0.08 | — | — | 0.18 | 0.07 | 0.42 | — | — | — | — | 0.08 | — | 0.83 | 99.2 |

TABLE 8-continued

| | maximum permeation rate ($\mu g/cm^2/hr$) | content (mass %) | | | | | | | | | | | | | amount of drug remained (%) |
| | | ropinirole | unknown compound | | | | | | | | | | | | |
| | | | column retention time (hr) | | | | | | | | | | | | |
| | | | 3.3 | 3.8 | 4.2 | 5.7 | 6.1 | 7.5 | 7.8 | 8.2 | 9.0 | 9.9 | 10.2 | 18.6 | total | |
|---|---|---|---|---|---|---|---|---|---|---|---|---|---|---|---|---|
| Comparative Example 15 | >0.45 | 92.9 | 2.31 | 0.16 | — | 0.36 | — | 0.39 | — | — | 0.11 | 0.18 | tr | — | 3.51 | 96.4 |
| Comparative Example 16 | >3.78 | 104.1 | — | — | — | — | — | — | — | — | — | — | — | 0.43 | 0.43 | 100.0 |

In Table 8, "tr" indicates that the detected amount was too small to be represented by a numerical value As apparent from the result shown in Table 8, it was verified that in the patch containing ropinirole, ropinirole tended to be decomposed if an acrylic-based adhesive was used as the adhesive base. Further, it was verified that if the adhesive agent layer contained SIS and sodium hydroxide in combination, the decomposition of ropinirole tended to be suppressed.

Examples 32 to 34

Patches were obtained in the same manner as in Example 1, except that the adhesive agent layer compositions had compositions shown in Table 9. Each of the patches obtained in Examples 32 to 34 was subjected to the skin permeation test and the evaluation test for stability over time. Table 10 shows the utilization ratio and the maximum permeation rate for 24 hours after the measurement was started, which were obtained in the skin permeation test, and the result of the evaluation test for stability over time.

TABLE 9

| Composition of adhesive agent layer composition (parts by mass) | Example 32 | Example 33 | Example 34 |
|---|---|---|---|
| SIS | 11.5 | 11.4 | 11.2 |
| PIB | 4.5 | 4.5 | 4.4 |
| alicyclic hydrocarbon resin | 43.0 | 42.6 | 42.4 |
| liquid paraffin | 12.0 | 11.9 | 11.8 |
| isopropyl palmitate | 10.0 | 10.0 | 10.0 |
| octyldodecanol | 3.0 | 3.0 | 3.0 |
| ropinirole hydrochloride | 15.0 | 15.0 | 15.0 |
| (parts by mass in terms of free ropinirole) | (13.2) | (13.2) | (13.2) |
| sodium hydroxide | 1.0 | 1.6 | 2.2 |

TABLE 10

| | maximum permeation rate ($\mu g/cm^2/hr$) | utilization ratio (%) | unknown compound content (mass %) (immediately after production) column retention time (hr) | | |
| | | | 5.4 | 8 | 12.7 |
|---|---|---|---|---|---|
| Example 32 | 44.2 | 65.5 | — | 0.04 | — |
| Example 33 | 66.7 | 76.8 | — | 0.04 | — |
| Example 34 | 42.5 | 58.4 | 0.08 | 0.38 | 0.17 |

As apparent from the result shown in Table 10, it was verified that the decomposition of ropinirole tended to be further suppressed if the adhesive agent layer contained SIS and sodium hydroxide in combination with the content of sodium hydroxide being 1 mol or less per 1 mol of ropinirole and/or a pharmaceutically acceptable salt thereof in terms of free ropinirole.

INDUSTRIAL APPLICABILITY

As has been described above, the present invention makes it possible to provide a ropinirole-containing patch having an excellent skin permeability of ropinirole and a sufficient adhesiveness, and a package of the ropinirole-containing patch, which has an excellent ropinirole stability over time.

REFERENCE SIGNS LIST

1: patch
2: support layer
3: adhesive agent layer
4: release sheet

The invention claimed is:

1. A ropinirole-comprising patch comprising: an adhesive agent layer comprising ropinirole, a ropinirole acid adduct, and 0.5 to 1.0 mol of a metal-ion containing desalting agent per 1.0 mol of the ropinirole and the ropinirole acid adduct in terms of free ropinirole; and
a support layer,
wherein the ropinirole and the ropinirole acid adduct is present in terms of free ropinirole in the adhesive agent layer in an amount of 8.8 to 13.2% by mass relative to a total mass of the adhesive agent layer.

2. The ropinirole-comprising patch of claim 1, wherein the adhesive agent layer further comprises 5 to 50 parts by mass of at least one compound selected from the group consisting of benzyl alcohol, oleyl alcohol, octyldodecanol, and dimethyl isosorbide, per 100 parts by mass of the ropinirole and the ropinirole acid adduct in terms of free ropinirole.

3. The ropinirole-comprising patch of claim 1, wherein the adhesive agent layer further comprises 10 to 150 parts by mass of at least one compound selected from the group consisting of isopropyl myristate, isopropyl palmitate, lauryl alcohol, glycerol monooleate, propylene glycol monolaurate, polyoxyethylene sorbitan monooleate, and lauric acid diethanolamide, per 100 parts by mass of the ropinirole and the ropinirole acid adduct in terms of free ropinirole.

4. The ropinirole-comprising patch of claim 1, wherein the adhesive agent layer further comprises 15 to 35% by mass of a rubber-base adhesive relative to the total mass of the adhesive agent layer.

5. The ropinirole-containing patch of claim 1, wherein the metal-ion containing desalting agent is sodium hydroxide.

6. A package, comprising:
the ropinirole-comprising patch of claim 1; and
a deoxidizer,
wherein the ropinirole-comprising patch and the deoxidizer are sealed in a packaging bag.

7. The ropinirole-comprising patch of claim 1, wherein the adhesive agent layer further comprises 5 to 50 parts by mass of benzyl alcohol per 100 parts by mass of the ropinirole and the ropinirole acid adduct in terms of free ropinirole.

8. The ropinirole-comprising patch of claim 1, wherein the adhesive agent layer further comprises 5 to 50 parts by mass of oleyl alcohol per 100 parts by mass of the ropinirole and the ropinirole acid adduct in terms of free ropinirole.

9. The ropinirole-comprising patch of claim 1, wherein the adhesive agent layer further comprises 5 to 50 parts by mass of octyldodecanol per 100 parts by mass of the ropinirole and the ropinirole acid adduct in terms of free ropinirole.

10. The ropinirole-comprising patch of claim 1, wherein the adhesive agent layer further comprises 5 to 50 parts by mass of dimethyl isosorbide per 100 parts by mass of the ropinirole and the ropinirole acid adduct in terms of free ropinirole.

11. The ropinirole-comprising patch of claim 1, wherein the adhesive agent layer further comprises 10 to 150 parts by mass of isopropyl myristate per 100 parts by mass of the ropinirole and the ropinirole acid adduct in terms of free ropinirole.

12. The ropinirole-comprising patch of claim 1, wherein the adhesive agent layer further comprises 10 to 150 parts by mass of isopropyl palmitate per 100 parts by mass of the ropinirole and the ropinirole acid adduct in terms of free ropinirole.

13. The ropinirole-comprising patch of claim 1, wherein the adhesive agent layer further comprises 10 to 150 parts by mass of lauryl alcohol per 100 parts by mass of the ropinirole and the ropinirole acid adduct in terms of free ropinirole.

14. The ropinirole-comprising patch of claim 1, wherein the adhesive agent layer further comprises 10 to 150 parts by mass of glycerol monooleate per 100 parts by mass of the ropinirole and the ropinirole acid adduct in terms of free ropinirole.

15. The ropinirole-comprising patch of claim 1, wherein the adhesive agent layer further comprises 10 to 150 parts by mass of propylene glycol monolaurate per 100 parts by mass of the ropinirole and the ropinirole acid adduct in terms of free ropinirole.

16. The ropinirole-comprising patch of claim 1, wherein the adhesive agent layer further comprises 10 to 150 parts by mass of polyoxyethylene sorbitan monoleate per 100 parts by mass of the ropinirole and the ropinirole acid adduct in terms of free ropinirole.

17. The ropinirole-comprising patch of claim 1, wherein the adhesive agent layer further comprises 10 to 150 parts by mass of lauric acid diethanolamide per 100 parts by mass of the ropinirole and the ropinirole acid adduct in terms of free ropinirole.

18. The ropinirole-comprising patch of claim 2, wherein the adhesive agent layer further comprises 10 to 150 parts by mass of at least one compound selected from the group consisting of isopropyl myristate, isopropyl palmitate, lauryl alcohol, glycerol monooleate, propylene glycol monolaurate, polyoxyethylene sorbitan monoleate, and lauric acid diethanolamide.

\* \* \* \* \*